US011332572B2

(12) United States Patent
Harada

(10) Patent No.: US 11,332,572 B2
(45) Date of Patent: May 17, 2022

(54) SPHERICAL POLYESTER RESIN PARTICLES AND METHOD FOR PRODUCING SAME

(71) Applicant: SEKISUI KASEI CO., LTD., Osaka (JP)

(72) Inventor: Ryosuke Harada, Osaka (JP)

(73) Assignee: SEKISUI KASEI CO., LTD., Osaka (JP)

( * ) Notice: Subject to any disclaimer, the term of this patent is extended or adjusted under 35 U.S.C. 154(b) by 205 days.

(21) Appl. No.: 16/493,422

(22) PCT Filed: Mar. 20, 2018

(86) PCT No.: PCT/JP2018/010927
§ 371 (c)(1),
(2) Date: Sep. 12, 2019

(87) PCT Pub. No.: WO2018/180738
PCT Pub. Date: Oct. 4, 2018

(65) Prior Publication Data
US 2020/0131306 A1 Apr. 30, 2020

(30) Foreign Application Priority Data
Mar. 31, 2017 (JP) .............................. JP2017-071628

(51) Int. Cl.
C08G 63/16 (2006.01)
A61K 8/02 (2006.01)
A61K 8/04 (2006.01)
A61K 8/85 (2006.01)
(Continued)

(52) U.S. Cl.
CPC .............. C08G 63/16 (2013.01); A61K 8/025 (2013.01); A61K 8/04 (2013.01); A61K 8/85 (2013.01);
(Continued)

(58) Field of Classification Search
None
See application file for complete search history.

(56) References Cited

U.S. PATENT DOCUMENTS 10,800,096 B2 * 10/2020 Iida ........................ C08L 71/00
2005/0272906 A1 12/2005 Cavaglia
(Continued)

FOREIGN PATENT DOCUMENTS

CN 1313513 5/2007
JP 52-18753 2/1977
(Continued)

OTHER PUBLICATIONS

International Search Report dated Jun. 26, 2018 in International Application No. PCT/JP2018/010927.
(Continued)

Primary Examiner — Jeffrey D Washville
(74) Attorney, Agent, or Firm — Wenderoth, Lind & Ponack, L.L.P.

(57) ABSTRACT

Spherical polyester-based resin particles characterized in that the spherical polyester-based resin particles contain a polyester-based resin and have a crystallinity of 20% or less and an average circularity of 0.96 or more. The spherical polyester-based resin particles according to the present invention can provide suitable resin particles as compounding agents for cosmetics such as foundation, antiperspirants, and skin scrubs; various agents such as matte coating agents for paints, rheology modifying agents, antiblocking agents, slipperiness-imparting agents, light diffusion agents, electroconductive agents, and diagnostic testing agents for medical use; and additives to molded articles such as automobile materials and construction materials.

11 Claims, 2 Drawing Sheets

(51) Int. Cl.
*A61Q 19/00* (2006.01)
*C08J 3/12* (2006.01)
*C08L 67/02* (2006.01)
*C09D 167/02* (2006.01)
*G02B 1/04* (2006.01)

(52) U.S. Cl.
CPC .............. *A61Q 19/00* (2013.01); *C08J 3/12* (2013.01); *C08L 67/02* (2013.01); *C09D 167/02* (2013.01); *G02B 1/04* (2013.01); *A61K 2800/10* (2013.01); *A61K 2800/262* (2013.01); *A61K 2800/654* (2013.01); *C08J 2367/02* (2013.01); *C08L 2201/10* (2013.01); *C08L 2201/56* (2013.01); *C08L 2203/16* (2013.01); *C08L 2205/18* (2013.01)

(56) References Cited

U.S. PATENT DOCUMENTS

| | | |
|---|---|---|
| 2006/0047102 A1 | 3/2006 | Weinhold et al. |
| 2011/0060110 A1 | 3/2011 | Shindo et al. |
| 2013/0183528 A1 | 7/2013 | Echigo et al. |
| 2013/0309497 A1 | 11/2013 | Takezaki et al. |

FOREIGN PATENT DOCUMENTS

| | | |
|---|---|---|
| JP | 59-11331 | 1/1984 |
| JP | 10-204162 | 8/1998 |
| JP | 2005-215492 | 8/2005 |
| JP | 2013-144745 | 7/2013 |
| JP | 2014-1403 | 1/2014 |
| JP | 2015-147947 | 8/2015 |
| WO | 2009/142010 | 11/2009 |
| WO | 2012/105140 | 8/2012 |

OTHER PUBLICATIONS

Suzuki et al., "Poly(ethylene terephthalate) Nanoparticles Prepared by $CO_2$ Laser Supersonic Atomization", Journal of Applied Polymer Science, 2014, pp. 1-6.

* cited by examiner

[FIG. 1]
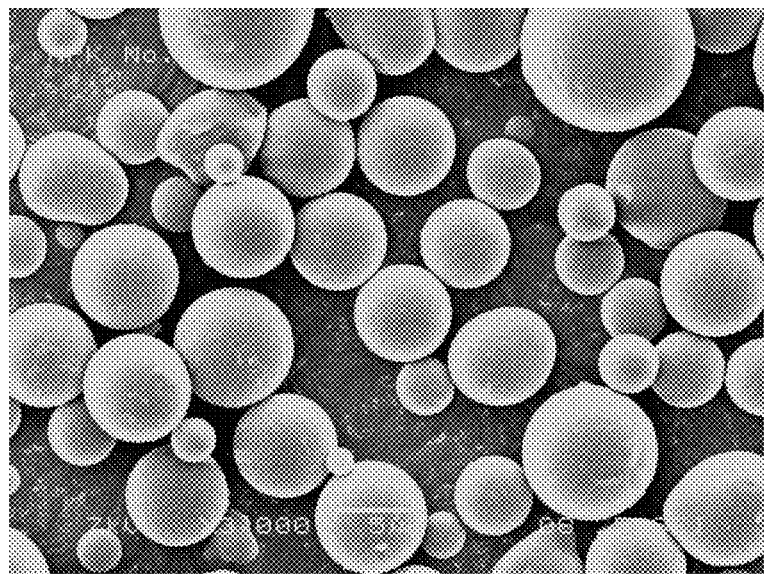
[FIG. 2]
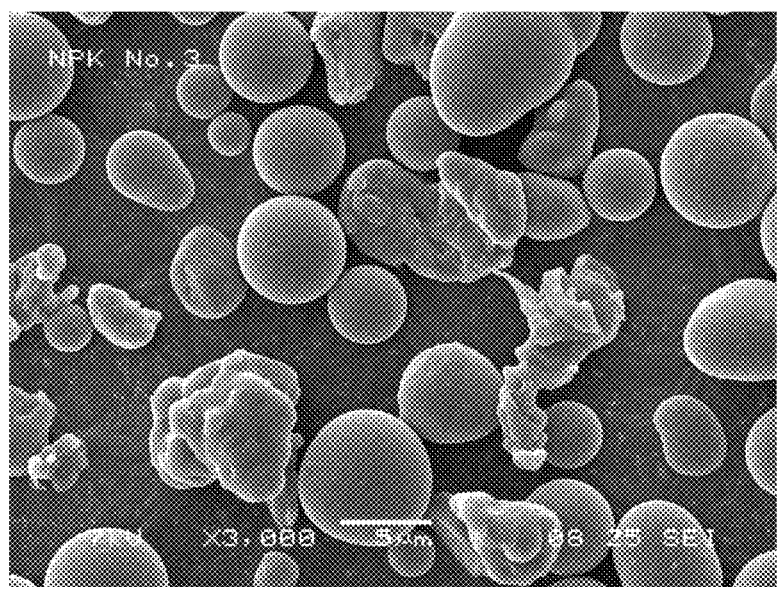

[FIG. 3]
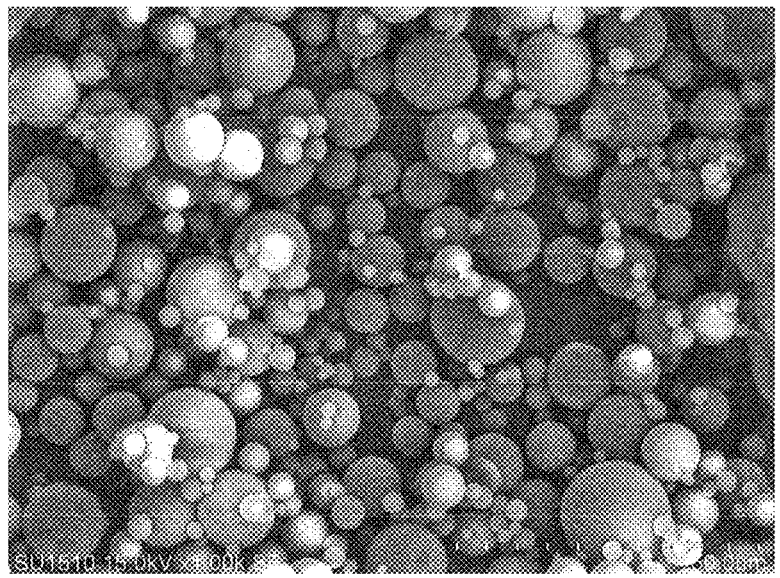
[FIG. 4]
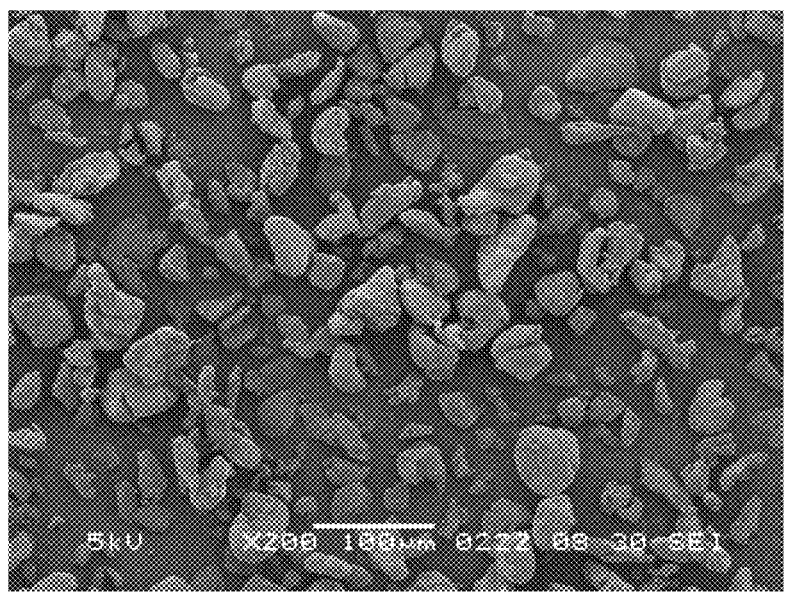

SPHERICAL POLYESTER RESIN PARTICLES AND METHOD FOR PRODUCING SAME

TECHNICAL FIELD

The present invention relates to spherical polyester-based resin particles and a method for production thereof.

BACKGROUND ART

Resin particles have been used in modifications and improvements in various kinds of materials, utilizing large specific surface areas and the structures of the particles. The main applications include applications such as compounding agents for cosmetics such as foundation, antiperspirants, and skin scrubs; various agents such as matte coating agents for paints, rheology modifying agents, antiblocking agents, slipperiness-imparting agents, light diffusion agents, electroconductive agents, and diagnostic testing agents for medical use; additives to molded articles such as automobile materials and construction materials, and the like.

For example, Patent Publication 1 discloses a method for producing beads for a light diffusion sheet, comprising fusing fine particles made of a transparent thermoplastic resin and subjecting the fused fine particles to a spherical formation treatment.

PRIOR ART REFERENCES

Patent Publications

Patent Publication 1: Japanese Patent Laid-Open No. 2013-144745

SUMMARY OF THE INVENTION

Problems to be Solved by the Invention

However, in the method for production of Patent Publication 1, although particles having high transparency are obtained when an acrylic resin is used, it can be hardly said that the crystallinity of the particles is sufficiently low when a polyester-based resin is used, so that further improvements have been in demand.

An object of the present invention is to provide spherical polyester-based resin particles having excellent transparency and a method for production thereof.

Means to Solve the Problems

The present invention relates to:
[1] spherical polyester-based resin particles characterized in that the spherical polyester-based resin particles contain a polyester-based resin, and have a crystallinity of 20% or less and an average circularity of 0.96 or more;
[2] a method for producing spherical polyester-based resin particles as defined in [1], comprising
melting polyester-based raw material resin particles having an intrinsic viscosity of 0.6 dl/g or less at a temperature higher than a melting point of the particles by 80° C. or more to form into spheres, and
cooling the particles after formation into spheres at a temperature equal to or lower than the melting point to solidify;
[3] a dispersion characterized in that the dispersion contains spherical polyester-based resin particles as defined in [1] and a binder, wherein the spherical polyester-based resin particles are dispersed as dispersed particles in the binder;
[4] an optical film characterized in that the optical film contains spherical polyester-based resin particles as defined in [1]; and
[5] cosmetics characterized in that the cosmetics contain spherical polyester-based resin particles as defined in [1].

Advantageous Effects of the Invention

According to the present invention, spherical polyester-based resin particles having excellent transparency and a method for production thereof can be provided.

BRIEF DESCRIPTION OF THE DRAWINGS

FIG. 1 A photograph of spherical polyester-based resin particles of Example 1.

FIG. 2 A photograph of spherical polyester-based resin particles of Example 2.

FIG. 3 A photograph of spherical polyester-based resin particles of Example 3.

FIG. 4 A photograph of spherical polyester-based resin particles of Comparative Example 1.

MODES FOR CARRYING OUT THE INVENTION (Spherical Polyester-Based Resin Particles)

The spherical polyester-based resin particles of the present invention contain a polyester-based resin, and have the following various physical properties.

(1) Various Physical Properties (a) Crystallinity

The crystallinity of the spherical polyester-based resin particles of the present invention is 20% or less, preferably 18% or less, more preferably 15% or less, and even more preferably 13% or less, from the viewpoint of transparency. The lower limit of the crystallinity can be, but not particularly limited to, 5% or more.

The crystallinity as used herein is measured by the following method.

The crystallinity of the spherical polyester-based resin particles is measured by a method described in JIS K7122: 2012 "Testing Methods for Heat of Transitions of Plastics." However, the sampling method and the temperature conditions are performed as follows. Using a differential scanning calorimeter Model DSC6220 manufactured by SII nanotechnology, about 10 mg sample is loaded to the bottom of an aluminum measurement vessel without leaving any voids, the contents are held at 30° C. for 2 minutes under a nitrogen gas flow rate of 20 mL/min, and the contents are heated from 30° C. to 290° C. at a rate of 10° C./min to obtain a DSC curve. Alumina is used as a standard substance at the time.

The crystallinity calculated in the present invention refers to a proportion calculated by dividing a difference of the amount of heat of fusion, J/g, obtained from the area of fusion peaks and the amount of heat of crystallinity, J/g, obtained from the area of crystal peaks, by a theoretical amount of heat of fusion of the perfect crystals of the polyester-based resins (e.g., in a case of polyethylene terephthalate: 140.1 J/g, in a case of polybutylene terephthalate: 145.5 J/g). The amount of heat of fusion and the amount of heat of crystallinity are calculated using the analyzing software attached to the apparatus.

Specifically, the amount of heat of fusion is calculated from a portion enclosed by a straight line that connects a point at which the DSC curve departs from the baseline at a lower temperature side and a point at which the DSC curve returns again to the baseline at a higher temperature side, and the DSC curve. The amount of heat of crystallinity is calculated from an area of a portion enclosed by a straight line that connects a point at which the DSC curve departs from the baseline at a lower temperature side and a point at which the DSC curve returns again to the baseline at a higher temperature side, and the DSC curve.

In other words, the crystallinity is calculated by the following formula.

$$\text{Crystallinity, \%} = \frac{\text{Amount of Heat of Fusion, J/g} - \text{Amount of Heat of Crystallinity, J/g}}{\text{Theoretical Amount of Heat of Fusion of Perfect Crystal, J/g}} \times 100$$

As to a partial amount of heat of fusion, when two or more peaks are present in the fusion peaks obtained, a boundary line is provided on the basis of the peak top temperatures of the projected portion existing among the fusion peaks, and each area obtained by dividing the amount of heat of fusion into a higher temperature side and a lower temperature side at the boundary line (partial amount of heat of fusion) is read-off.

(b) Circularity

The average circularity of the spherical polyester-based resin particles of the present invention is 0.96 or more, preferably 0.97 or more, more preferably 0.98 or more, and most preferably 1, from the viewpoint of light diffusibility, flowability, and scratch resistance.

In addition, the spherical polyester-based resin particles of the present invention have a proportion of particles having a circularity of 0.90 or more of preferably 10% by number or less, more preferably 5% by number or less, even more preferably 3% by number or less, and most preferably 0% by number, from the viewpoint of light diffusibility, flowability, and scratch resistance.

The circularity as used herein is measured by the following method.

The circularity of the spherical polyester-based resin particles is measured using Flow Particle Image Analyzer under the trade name of "FPIA(registered trademark)-3000S, manufactured by Sysmex Corporation.

As a specific method for measurement, 0.05 g of an alkylbenzenesulfonate is added as a dispersant to 20 mL of ion-exchanged water to give an aqueous surfactant solution. Thereafter, 0.2 g of resin particles to be measured are added to the above aqueous surfactant solution, and the resin particles are irradiated with ultrasonic waves for 5 minutes using an ultrasonic dispersing machine "BRANSON SONIFIER 450," manufactured by BRANSON having an output power of 400 W and a frequency of 20 kHz as a dispersing machine, to carry out a dispersion treatment of dispersing the resin particles in the aqueous surfactant solution to give a dispersion to be measured.

The above Flow Particle Image Analyzer mounted with a standard objective lens (10×) is used for the measurement, and a particle sheath under the trade name of "PSE-900A" manufactured by Sysmex Corporation is used as a sheath fluid to be used in the above Flow Particle Image Analyzer. The dispersion to be measured which is adjusted in accordance with the above procedures is introduced into the above Flow Particle Image Analyzer, and measured under the following measurement conditions.

Measurement mode: LPF or HPF measurement mode (appropriately selected according to particle sizes. As a measure, in a case of particle sizes of 8 μm or less, HPF measurement mode is selected, and in a case of particle sizes of 8 μm or more, LPF measurement mode is selected.) Number of particles to be measured: 10,000 particles Upon the measurement, prior to the beginning of the measurement, an automatic focus adjustment of the above Flow Particle Image Analyzer is carried out using a suspension of standard polymer particles, for example, "5200A" manufactured by Thermo Fisher Scientific, a solution prepared by diluting standard polystyrene particles with ion-exchanged water. Here, the circularity is a value calculated by dividing a circumferential length calculated from a diameter of a true circle having the same projected area as the image of photographed resin particles by a circumferential length of the image of photographed resin particles. The average circularity is a value calculated by dividing a total of circularities of individual particles by the frequencies on the number basis. The proportion of the number of particles having a circularity of 0.90 or less is calculated from the data of frequency on the number basis in the intervals of 0.010 measured by the above measurement, for example, 0.980 or more and less than 0.990. Upon the data analysis, the measurements are carried out by setting the following ranges.

Measurement ranges of particle sizes: from 0.5 μm to 200 μm Measurement ranges of circularity of particles: from 0.2 to 1.0

(c) Volume-Average Particle Size

The volume-average particle size of the spherical polyester-based resin particles of the present invention is preferably from 1 to 300 μm, more preferably from 1 to 100 μm, and even more preferably from 3 to 50 μm, because the optical film having excellent light diffusibility is easily obtained when used as a coating.

The volume-average particle size as used herein is measured in accordance with the following method.

The volume-average particle size of the spherical polyester-based resin particles is measured with Coulter Multisizer™ 3, a measurement apparatus manufactured by Beckman Coulter, Inc. The measurement is to be carried out with an aperture calibrated in accordance with the Multisizer™ 3 User's Manual published by Beckman Coulter, Inc.

Here, the aperture used in the measurement is appropriately selected depending upon the sizes of spherical polyester-based resin particles to be measured. Current (aperture current) and Gain (gain) are appropriately set depending upon the sizes of the apertures selected. For example, in a case where an aperture having a size of 50 μm is selected, the Current (aperture current) is set at −800, and Gain (gain) at 4.

As the samples for the measurement, 0.1 g of spherical polyester-based resin particles are dispersed in 10 ml of a 0.1% by mass aqueous nonionic surfactant solution using a touch mixer "TOUCH MIXER MT-31" manufactured by Yamato Scientific Co., Ltd. and an ultrasonic cleaner "ULTRASONIC CLEANER VS-150" manufactured by VELVO-CLEAR to give a dispersion, and the dispersion is used. During the measurement, a beaker is previously gently stirred so as not to allow the entry of bubbles, and the measurement is terminated at a time point when 100,000 particles of the spherical polyester-based resin particles are measured. The volume-average particle size of the spherical polyester-based resin particles is an arithmetic means in the particle size distribution on the volume basis of 100,000 particles.

(d) Refractive Index

The refractive index of the spherical polyester-based resin particles of the present invention is preferably from 1.560 to 1.590, more preferably from 1.565 to 1.585, and even more preferably from 1.570 to 1.580, because the optical film having excellent light diffusibility is easily obtained when used as a coating.

The refractive index as used herein is measured by a liquid immersion method.

First, spherical polyester-based resin particles are placed on a slide glass, and a refractive index liquid (Cargille standard refractive index liquids manufactured by CARGILLE, a plurality of refractive index liquids each having a refractive index nD25 of from 1.560 to 1.600 are prepared with a difference in the refractive indices of 0.002) is dropped thereto. Moreover, the spherical polyester-based resin particles and the refractive index liquid are thoroughly mixed, and the contours of the particles are observed with an optical microscope from an upper side, while irradiating light of high-pressure sodium lamp NX35 having a central wavelength of 589 nm manufactured by IWASAKI ELECTRIC CO., LTD. from the bottom. Moreover, a case where the contours are not visible is judged such that the refractive index of the refractive index liquid is of the same level as the refractive index of the spherical polyester-based resin particles. Here, there are no particular problems in the observations with the optical microscope so long as the observations are made in the magnifications at which the contours of the spherical polyester-based resin particles can be confirmed, and the observation magnifications of 500 folds or so are appropriate for particles having particle sizes of 5 μm. By the above procedures, the more the refractive indices of the spherical polyester-based resin particles and the refractive index liquid approximate each other, the contours of the spherical polyester-based resin particles are less likely to be visible, so that it is judged that the refractive index of the refractive index liquid with which the contours of the spherical polyester-based resin particles are less likely to be defined is equal to the refractive index of the spherical polyester-based resin particles.

In addition, when there are no differences in visibility of the spherical polyester-based resin particles between two kinds of refractive index liquids with a difference in refractive indices of 0.002, it is judged that an intermediate value of these two kinds of the refractive index liquids is a refractive index of the spherical polyester-based resin particles. For example, in a case where tests are conducted with each of the refractive index liquids having refractive indices of 1.554 and 1.556, when there are no differences in visibility of the spherical polyester-based resin particles between both the refractive index liquids, it is judged that an intermediate value 1.555 of these refractive index liquids is a refractive index of the spherical polyester-based resin particles.

Here, in the above measurement, the measurements are carried out in a test room under the environment of an air temperature of from 22° C. to 24° C.

(e) Mass Loss Ratio

It is preferable that the spherical polyester-based resin particles of the present invention have a mass loss ratio after heating at 200° C. for 2 hours of 3% or less, from the viewpoint of suppressing the bleed out of the volatile components contained in the resin particles to the coating surface, and the mass loss ratio is more preferably 2% or less, and further 1% or less.

(f) Water

In addition, it is preferable that the spherical polyester-based resin particles of the present invention have water contained in the resin particles within the range of from 0.01% by mass to 0.5% by mass, from the viewpoint of homogeneous dispersibility in a solvent, and more preferably within the range of from 0.05% by mass to 0.3% by mass. Here, the water is measured in accordance with Karl-Fischer method.

(2) Polyester-Based Resin

The polyester-based resin in the present invention includes, but not particularly limited to, aromatic polyester-based resins such as polyethylene terephthalate, polybutylene terephthalate, polyethylene naphthalate, polybutylene naphthalate, and polytrimethylene terephthalate; and aliphatic polyester-based resins such as polyethylene succinate, polybutylene succinate, polyhydroxyalkanoates, and polyhydroxybutyrate. Among them, when used as a compounding agent for optical films, polyethylene terephthalate and polybutylene terephthalate are preferred, from the viewpoint of obtaining spherical polyester resin particles having high transparency. In addition, when used as a compounding agent for cosmetics, such as foundation, skin scrubs, and antiperspirants, polybutylene succinate and polyhydroxyalkanoates are preferred, from the viewpoint of obtaining spherical polyester-based resin particles having a small difference in refractive indices with liquid components in the cosmetics. Here, it is preferable that the polyester-based resin is a homopolymer, but the polyester-based resin may be a copolymer using another component such as a dicarboxylic acid component or a glycol component, or the polyester-based resin may be a blend polymer in which other condensed resin is mixed.

(3) Other Additives

The spherical polyester-based resin particles of the present invention may optionally contain other additives so long as they do not affect the performance. Other additives include plasticizers, flame retardants, flame retarding aids, antistatic agents, spreading agents, cell controlling agents, fillers, colorants, weatherproof agents, anti-aging resistors, lubricants, anti-clouding agents, perfumes, and the like. Here, when used as a compounding agent for optical films, transparent particles without containing colorants such as dyes and pigments are preferred.

(Method for Producing Spherical Polyester-Based Resin Particles)

The method for producing spherical polyester-based resin particles of the present invention comprises melting polyester-based raw material resin particles having an intrinsic viscosity of 0.6 dl/g or less at a temperature higher than a melting point of the particles by 80° C. or more to form into spheres, and cooling the particles after formation into spheres at a temperature equal to or lower than the melting point to solidify.

Although the mechanisms for obtaining spherical polyester-based resin particles having excellent transparency according to the method for production are not ascertained, the polyester-based raw material resin particles having the above intrinsic viscosity are melted at a temperature higher than a melting point of the particles by 80° C. or more, so that the movements of the molecular chain become active. In addition, a surface tension is acted to form into spheres. Subsequently, the temperature is lowered to a temperature equal to or lower than the melting point to solidify before the molecular chains form crystals, whereby the crystallinity can be assumed to be controlled at a low level.

(Melting Step)

The polyester-based raw material resin particles used in the melting step have an intrinsic viscosity of 0.6 dl/g or less, preferably 0.55 dl/g or less, and more preferably 0.5 dl/g or less, from the viewpoint of lowering the crystallinity of the particles after melting and from the viewpoint of increasing the circularity, and an intrinsic viscosity of preferably 0.2 dl/g or more, from the viewpoint of having sufficient strength of the particles after melting.

The intrinsic viscosity as used herein is measured in accordance with the following method.

The intrinsic viscosity of the polyester-based raw material resin particles is calculated from a solution viscosity which is measured by heating 0.5 g of polyester-based raw material resin particles in 100 ml of a tetrachloroethane/phenol=50/50 (mass ratio) mixed solution to dissolve, and then cooling the solution to measure at 25° C.

The crystallinity of the polyester-based raw material resin particles used in the melting step is preferably from 30 to 50%, and more preferably from 35 to 45%, from the viewpoint of obtaining particles having a high circularity. The crystallinity of the polyester-based raw material resin particles is measured in the same manner as in the spherical polyester-based resin particles.

The average circularity of the polyester-based raw material resin particles used in the melting step is preferably from 0.50 to 1.00, and more preferably from 0.60 to 1.00, from the viewpoint of obtaining particles having a high circularity. The circularity of the polyester-based raw material resin particles is measured in the same manner as in the spherical polyester-based resin particles.

The volume-average particle size of the polyester-based raw material resin particles used in the melting step is preferably from 1 to 50 μm, and more preferably from 1 to 30 μm, from the viewpoint of easily giving a sufficient amount of heat to the resin particles, and obtaining particles having a high circularity. The volume-average particle size of the polyester-based raw material resin particles is measured in the same manner as in the spherical polyester-based resin particles.

Here, the polyester-based raw material resin particles used in the melting step can be prepared, for example, by the following method.

(Preparation Example of Polyester-Based Raw Material Resin Particles)

The method for production includes contacting a polyester-based raw material resin with a glycol ether-based solvent, and pulverizing the contents after the contact.

In the contacting step, a polyester-based raw material resin is heated to a temperature equal to or higher than a crystallization temperature of the polyester-based raw material resin in the presence of a glycol ether-based solvent, and thereafter cooling the mixture. Here, as the polyester-based raw material resin, the same resins as those exemplified above can be used. The glycol ether-based solvent includes 3-methoxy-3-methyl-1-butanol and the like.

In the pulverizing step, methods using various known mills can be used. The contents are roughly pulverized with, for example, a pulverizer such as a crusher, a hammer-mill, a feather mill, or a Labo Millser, and thereafter can be further finely pulverized with, for example, a mechanical pulverizer such as Kryptron system manufactured by Kawasaki Heavy Industries, Ltd., Super Rotor manufactured by NIS SHIN ENGINEERING, INC., Turbo Mill manufactured by Turbo Kogyo Co., Ltd., or a pulverizer manufactured by Hosokawa Micron Corporation, or a fine pulverizer according to an air jet system such as a Current Jet Mill or a Super Jet Mill manufactured by NIS SHIN ENGINEERING, INC. Subsequently, the pulverized products can be further optionally classified with a classifier or a siever such an inertial classification system Elbow-jet manufactured by Nittetsu Mining Co., Ltd., a centrifugal classification system Turboplex manufactured by Hosokawa Micron Corporation, TSP Separator manufactured by Hosokawa Micron Corporation, or FACULTY manufactured by Hosokawa Micron Corporation.

The melting step includes melting the polyester-based raw material resin particles at a temperature higher than a melting point of the particles by 80° C. or more, preferably by 100° C. or more, and more preferably by 150° C. or more, to form into spheres, from the viewpoint of lowering the crystallinity of the particles after melting, and from the viewpoint of increasing the circularity. In addition, it is preferable that the temperature of the melting step is a temperature equal to or lower than a melting point by 300° C. or more, from the viewpoint of suppressing the lowering in the strength due to the deterioration of the resin particles and the loss of transparency. For example, when a polyethylene terephthalate having a melting point of 250° C. is used as the polyester-based raw material resin particles, it is preferable that the particles are melted at a temperature of from 330° to 550° C. to form into spheres. Here, the melting point of the polyester-based raw material resin particles as used herein is a melting point in the heating process (heating rate: 20° C./min), as obtained by DSC, which includes, in accordance with a method based on MS K-7121(1999), heating raw material resin particles from 25° C. to 300° C. at a heating rate of 20° C./minute (1st RUN); holding in that state for 5 minutes, rapidly cooling to a temperature of 25° C. or lower, and heating again from room temperature to 300° C. at a heating rate of 20° C./minute, in which a temperature of a peak top in the crystal fusion peaks of 2nd RUN is defined as a melting point of the resin particles.

The treatment time in the melting step is preferably 1 second or less, from the viewpoint of suppressing the degradation of the resin particles.

In the melting step, a known heated air surface modifying apparatus or the like can be used, including METEOR RAINBOW MR Type manufactured by Nippon Pneumatics Mfg. Co., Ltd. or the like.

When the heated air surface modifying apparatus is used in the melting step, the treatment temperature is the temperature of the heated air, and the air flow of the heated air is preferably from 10 to 150 L/g, more preferably from 12 to 120 L/g, and even more preferably from 15 to 100 L/g, from the viewpoint of obtaining particles having a high circularity.

(Cooling Step)

In the cooling step, the particles after formation into spheres in the above melting step are solidified at a temperature equal to or lower than a melting point of the particles, and preferably a temperature lower than a melting point of the particles by 100° C. or more. The lower limit of the cooling temperature can be, but not particularly limited to, set to, for example, 0° C. or higher. A cooling means includes, but not particularly limited to, besides the solidification in a room temperature atmosphere, a method of solidification by allowing particles to pass through a pipe equipped with a cooling jacket, and the like.

Thus, spherical polyester-based resin particles of the present invention are obtained.

Since the spherical polyester-based resin particles of the present invention have excellent transparency, the spherical polyester-based resin particles can be suitably used in applications such as compounding agents for cosmetics such as foundation, antiperspirants, and skin scrubs; various agents such as matte coating agents for paints, rheology modifying agents, antiblocking agents, slipperiness-imparting agents, light diffusion agents, electroconductive agents, and diagnostic testing agents for medical use; additives to molded articles such as automobile materials and construction materials.

The spherical polyester-based resin particles of the present invention are suitably provided as an embodiment of a dispersion. A dispersion described above contains spherical polyester-based resin particles of the present invention and a binder, in which the spherical polyester-based resin particles of the present invention are dispersed as dispersed particles in a binder.

The binder includes acrylic resins, alkyd resins, polyester resins, polyurethane resins, chlorinated polyolefin resins, amorphous polyolefin resins, ultraviolet curing resins, and the like.

The dispersion can further optionally contain a crosslinking agent, a solvent, a coating surface adjusting agent, a flowability adjusting agent, an ultraviolet absorbent, a photostabilizer, a curing catalyst, an extender pigment, a coloring pigment, a metallic pigment, a mica powder pigment, a dye, or the like, in accordance with the applications to be used.

Since the dispersion containing spherical polyester-based resin particles of the present invention has excellent light diffusibility, the dispersion can be suitably used as optical films such as light diffusion sheets, matte coating agents for paints, or the like. For example, by applying the above dispersion to a substrate film for an optical use, an optical film containing spherical polyester-based resin particles of the present invention can be produced, and the optical film has excellent light diffusibility.

When the dispersion containing spherical polyester-based resin particles of the present invention is used in applications for an optical film, the mass ratio of the spherical polyester-based resin particles to the binder in the dispersion, particles/binder, is preferably from 1/10 to 1/1, and more preferably from 1/5 to 1/2, from the viewpoint of obtaining an optical film having excellent light diffusibility.

[Optical Film]

The spherical polyester-based resin particles of the present invention can be used as a light diffusion agent for optical films. The optical film of the present invention comprises a substrate film at least one of which side is coated with a dispersion containing the above spherical polyester-based resin particles of the present invention to form a film. The optical film of the present invention as described above can be utilized as anti-dazzle films, light diffusion films, and the like.

The materials of the above substrate film are not particularly limited so long as the materials have transparency, and the materials include, for example, polyester-based resins such as polyethylene terephthalate, triacetyl cellulose resins, polystyrene-based resins, polycarbonate-based resins, cycloolefin-based resins, and the like.

[Cosmetics]

Further, the spherical polyester-based resin particles of the present invention can be used as a compounding agent for cosmetics. The cosmetics of the present invention contain spherical polyester-based resin particles of the present invention. The content of the spherical polyester-based resin particles in the cosmetics can be properly set depending upon the kinds of the cosmetics, and the content is preferably within the range of from 1 to 80% by mass, and more preferably within the range of from 5 to 70% by mass.

The cosmetics are not particularly limited so long as the effects are exhibited by the containment of the above spherical polyester-based resin particles, and include, for example, liquid-based cosmetics such as pre-shave lotions, body lotions, make-up lotions, make-up creams, milky lotions, body shampoos, and antiperspirants; cleansing make-ups such as soaps and scrub facial washing agents; facial packs; shaving creams; face powders; foundation; lipsticks; lip creams; cheek blushers; eyebrow-eye make-ups; manicure make-ups; cosmetics for hairwash; hairdyes; hairdressing; fragrant cosmetics; toothpastes; bath agents; sunscreen articles; suntan articles; cosmetics for bodies such as body powders and baby powders; and the like. Among them, the liquid-based cosmetics and cleansing make-ups are preferred.

In addition, these cosmetics can be formulated with a generally used main agent or additive according to its purpose, within the range that would not impair the effects of the present invention. The main agent or additive as described above includes, for example, water; lower alcohols, i.e., alcohols having 5 or less carbon atoms; fats and oils and waxes; hydrocarbons; higher aliphatic acids, i.e., aliphatic acids having 12 or more carbon atoms; higher alcohols, i.e., alcohols having 6 or more carbon atoms; sterols; fatty acid esters such as cetyl 2-ethylhexanoate; metallic soaps; moisturizing agents; surfactants such as sorbitan sesquioleate; polymer compounds; clay minerals, i.e., components which have the several kinds of functions in one, such as extender pigments and adsorbents, talc, mica, etc.; colorant raw materials such as titanium oxide, red iron oxide, yellow iron oxide, and black iron oxide; perfume; preservatives and bactericidal agents; antioxidants; ultraviolet absorbents; other resin particles such as silicone-based particles and polystyrene particles; specialized compounding additives; and the like.

EXAMPLES

The present invention will be described more specifically hereinbelow by means of Examples, without intending to limit the present invention to the following Examples.

Production Example 1 of Polyester-Based Raw Material Resin Particles Contacting Step Fifty grams of pellets of polyethylene terephthalate under the trade name of GLOBIO BCB80 manufactured by Honam Petrochemical Corp. as a polyester-based raw material resin and 100 g of 3-methoxy-3-methyl-1-butanol under the trade name of SOLFIT manufactured by Kuraray Co., Ltd. as a glycol ether-based solvent were supplied into a 300-ml autoclave equipped with a stirrer, and the contents were stirred for 2 hours under the conditions of 185° C. Two hours later, the contents were rapidly cooled to room temperature, and the contents were subjected to steps of separation by filtration, washing of the residues with water, and drying with an oven at 80° C., to give 49 g of pellets of polyester-based raw material resin that were contacted with the solvent.

Pulverizing Step

The above contacted polyester-based raw material resin was roughly pulverized with a Labo Millser, a small-scaled pulverizer Labo Millser PLUS LMPLUS of OSAKA CHEMICAL Co., Ltd., and then subjected to a fine pulverization treatment with a Current Jet-Mill CJ-10, manufactured by NISSHIN ENGINEERING, INC. having a milling air pressure of 0.5 MPa. As a result, fine polyester-based raw material resin particles having a volume-average particle size of 7.5 µm, a crystallinity of 38%, an average circularity of 0.89, and an intrinsic viscosity of 0.4 dl/g were obtained.

Production Example 2 of Polyester-Based Raw Material Resin Particles

The same procedures as in Production Example 1 were carried out except that a polybutylene terephthalate under the trade name of TORAYCON PBT 1401X06 manufactured by Toray Industries, Inc. was used as a polyester-based raw material resin, and that in the contacting step the contents were stirred for 2 hours in the autoclave under the conditions of 190° C., to give fine polyester-based raw material resin particles having a volume-average particle size of 14.5 µm, a crystallinity of 41%, an average circularity of 0.88, and an intrinsic viscosity of 0.45 dl/g.

Production Example 3 of Polyester-Based Raw Material Resin Particles

The same procedures as in Production Example 1 were carried out except that the contacting step was not carried out, and that a polyethylene terephthalate under the trade name of "CH611" manufactured by The Far Eastern Industry was used in place of the contacted polyester-based raw material resin, to give fine polyester-based raw material resin particles having a volume-average particle size of 30 µm, a crystallinity of 39%, an average circularity of 0.87, and an intrinsic viscosity of 1.05 dl/g.

Examples 1 to 3 and Comparative Example 1

The polyester-based raw material resin particles as listed in Table 1 were melted under the conditions as listed in Table 1 using a heated air surface modifying apparatus METEOR RAINBOW MR-10 manufactured by Nippon Pneumatics Mfg. Co., Ltd. and subjected to a treatment of forming into spheres, and the formed resin particles were solidified in the atmosphere of room temperature (25° C.), to give spherical polyester-based resin particles. Here, the melting treatment time was 1 second or less. The spherical polyester-based resin particles obtained were photographed with a scanning electron microscope Model JSM-6360LV, manufactured by JEOL, Ltd. The photographs are shown in FIGS. 1 to 4.

With respect to the spherical polyester-based resin particles of each of Examples and Comparative Example, the crystallinity, the average circularity, the proportion of particles having a circularity of 0.90 or less, and the volume-average particle size were measured. The results are shown in Table 1. Here, the measurement methods for each of the physical properties are as described above.

TABLE 1

| | | Polyester-Based Raw Material Resin Particles | | | | Melting Step | | Polyester-Based Resin Particles | | | |
|---|---|---|---|---|---|---|---|---|---|---|---|
| | Prod. Ex. | Crystal- linity % | Average Circu- larity — | Volume- Average Particle Size µm | Intrinsic Viscosity dl/g | Heated Air Temp. ° C. | Air Flow of Heated Air L/g | Crystal- linity % | Average Circu- larity — | Proportion of Particles Having Circularity of 0.90 or Less % by Number | Volume- Average Particle Size µm |
| Ex. 1 | 1 | 38 | 0.89 | 7.5 | 0.4 | 450 | 70 | 11 | 0.98 | 1.6 | 6 |
| Ex. 2 | 1 | 38 | 0.89 | 7.5 | 0.4 | 350 | 70 | 13 | 0.97 | 5.3 | 6 |
| Ex. 3 | 2 | 41 | 0.88 | 14.5 | 0.45 | 450 | 40 | 12 | 0.98 | 1.8 | 15 |
| Comp. Ex. 1 | 3 | 39 | 0.87 | 30 | 1.05 | 450 | 70 | 38 | 0.92 | 28.5 | 30 |

While the polyester-based raw material resin particles having the same levels of the crystallinity and the average circularity were used, in Examples 1 to 3 where polyester-based raw material resin particles having an intrinsic viscosity of 0.6 dl/g or less were used, the spherical polyester-based resin particles obtained had a low crystallinity and a high circularity. On the other hand, in Comparative Example 1 where polyester-based raw material resin particles having an intrinsic viscosity of 1.05 were used, the spherical polyester-based resin particles obtained had a high crystallinity and a low circularity.

In addition, when a refractive index of the spherical polyester-based resin particles of Example 1 was confirmed by a liquid immersion method, the particle contours would be invisible in a refractive index liquid having a refractive index of 1.572, and the particle immersion liquid was also transparent. On the other hand, when a refractive index was confirmed between 1.56 and 1.60 by a liquid immersion method for the spherical polyester-based resin particles of Comparative Example 1 with an increment of 0.02, no liquids were found that make the particle contours invisible. Therefore, it can be seen that Example 1 is more excellent in transparency than Comparative Example 1. Here, Examples 2 and 3 also were excellent in transparency in the same manner as in Example 1.

As to the spherical polyester-based resin particles of Example 1 and Comparative Example 1, the water content and the mass loss ratio were measured. Using TGA apparatus TG/DTA6200 manufactured by Seiko Instruments Inc., the measurements were made in which the particles were heated from 40° to 200° C. at a rate of 10°/minute in a nitrogen atmosphere, and after having reached 200° C., the temperature was held thereat for 2 hours, and a mass loss ratio was calculated. The results are shown in Table 2.

TABLE 2

|  | Mass Loss Ratio, % | Water Content, % by Mass |
|---|---|---|
| Example 1 | 0.91 | 0.16 |
| Comparative Example 1 | 0.82 | 0.17 |

Production Example 1 of Coating Materials for PET Film

The amount 7.5 parts by mass of spherical polyester-based resin particles obtained in Example 1, 30 parts by mass of an acrylic resin under the product name of ACRYDIC A811 manufactured by DIC Corporation, 10 parts by mass of a crosslinking agent under the product name of VM-D manufactured by DIC Corporation, and 50 parts by mass of butyl acetate as a solvent were mixed for 3 minutes with an agitator-defoaming apparatus, and the contents were defoamed for 1 minute, to give a dispersion containing spherical polyester-based resin particles. The dispersion obtained was applied to a PET film having a thickness of 125 μm using a coating apparatus to which a blade having a clearance of 50 μm was set, and then dried at 70° C. for 10 minutes, to give a film. The haze of the film obtained was 78.6%, and a total light transmittance was 90.8%.

The haze and the total light transmittance were measured in accordance with JIS K 7361-1 using a haze meter under the trade name of "NDH4000" manufactured by NIPPON DENSHOKU INDUSTRIES CO., LTD.

Production Example of Paint

Two parts by mass of each of the resin particles obtained in Example 1 and 20 parts by mass of a commercially available acrylic aqueous glossy paint under the trade name of Super Hit manufactured by Kanpe Hapio Co., Ltd. were mixed for 3 minutes with an agitator-defoaming apparatus, and the contents were defoamed for 1 minute, to give a paint.

The paint obtained was applied to an ABS resin (acrylonitrile-butadiene-styrene resin) plate using a coater apparatus to which a blade having a clearance of 75 μm was set, to give a coat film. The gloss (60°) of the coat film obtained as measured by using GLOSS CHECKER IG-330 manufactured by HORIBA, Ltd. was 14.

Production Example of Cosmetics

Production of Makeup Milky Lotion

Production Method

First, stearic acid, cetyl alcohol, Vaseline, a liquid paraffin, and polyethylene monooleate ester are heated to melt, resin particles are added and mixed thereto, and the mixture is held at a temperature of 70° C. (oil phase). In addition, polyethylene glycol and triethanolamine are added to purified water, and a mixture is heated to melt, and held at a temperature of 70° C. (aqueous phase). The oil phase is added to the aqueous phase, and the mixture is subjected to preliminary emulsification, and thereafter homogeneously emulsified with a homomixer. After emulsification, the emulsion is cooled to 30° C. while stirring, to give a makeup milky lotion.

Formulation Amounts

| Resin particles obtained in Example 1 | 10.0 parts by mass |
|---|---|
| Stearic acid | 2.5 parts by mass |
| Cetyl alcohol | 1.5 parts by mass |
| Vaseline | 5.0 parts by mass |
| Liquid paraffin | 10.0 parts by mass |
| Polyethylene(10 mol) monooleate ester | 2.0 parts by mass |
| Polyethylene Glycol 1500 | 3.0 parts by mass |
| Triethanolamine | 1.0 part by mass |
| Purified Water | 64.5 parts by mass |
| Perfume | 0.5 parts by mass |
| Preservative | Proper amounts |

INDUSTRIAL APPLICABILITY

The spherical polyester-based resin particles according to the present invention can provide suitable resin particles as compounding agents for cosmetics such as foundation, antiperspirants, and skin scrubs; various agents such as matte coating agents for paints, rheology modifying agents, antiblocking agents, slipperiness-imparting agents, light diffusion agents, electroconductive agents, and diagnostic testing agents for medical use; additives to molded articles such as automobile materials and construction materials, and the like.

The invention claimed is:

1. Spherical polyester-based resin particles wherein the spherical polyester-based resin particles comprise a polyester-based resin and have a crystallinity of 20% or less and an average circularity of 0.96 or more, wherein circularity is a value calculated by dividing a circumferential length calculated from a diameter of a true circle, and wherein the average circularity is a value calculated by dividing a total of circularities of individual particles by the frequencies on the number basis.

2. The spherical polyester-based resin particles according to claim 1, wherein the mass loss ratio after heating at 200° C. for two hours is 3% or less.

3. The spherical polyester-based resin particles according to claim 1, wherein the polyester-based resin is a polyethylene terephthalate or a polybutylene terephthalate.

4. The spherical polyester-based resin particles according to claim 1, wherein the proportion of the particles having a circularity of 0.90 or less is 10% by number or less.

5. The spherical polyester-based resin particles according to claim 1, wherein the spherical polyester-based resin particles are compounding agents for optical films.

6. The spherical polyester-based resin particles according to claim 1, wherein the spherical polyester-based resin particles are compounding agents for paints.

7. The spherical polyester-based resin particles according to claim 1, wherein the spherical polyester-based resin particles are compounding agents for cosmetics.

8. A method for producing spherical polyester-based resin particles as defined in claim 1, comprising
melting polyester-based raw material resin particles having an intrinsic viscosity of 0.6 dl/g or less at a temperature higher than a melting point of the particles by 80° C. or more to form into spheres, and
cooling the particles after formation into spheres at a temperature equal to or lower than the melting point to solidify.

9. A dispersion wherein the dispersion comprises spherical polyester-based resin particles as defined in claim 1 and a binder, wherein the spherical polyester-based resin particles are dispersed as dispersed particles in the binder.

10. An optical film wherein the optical film comprises spherical polyester-based resin particles as defined in claim 1.

11. Cosmetics wherein the cosmetics comprise spherical polyester-based resin particles as defined in claim 1.

* * * * *